US00PP17559P2

(12) United States Plant Patent
Vanderberg

(10) Patent No.: US PP17,559 P2
(45) Date of Patent: Apr. 3, 2007

(54) CARNATION PLANT NAMED 'YODER SHOW'

(50) Latin Name: *Dianthus caryophyllus*
Varietal Denomination: Yoder Show

(75) Inventor: Cornelis P. Vanderberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/212,389

(22) Filed: Aug. 26, 2005

(51) Int. Cl.
*A01H 5/00* (2006.01)

(52) U.S. Cl. ..... Plt./272
(58) Field of Classification Search ..... Plt./272
See application file for complete search history.

*Primary Examiner*—Kent Bell
(74) *Attorney, Agent, or Firm*—C. A. Whealy

(57) ABSTRACT

A distinct cultivar of Carnation plant named 'Yoder Show', characterized by its large white-colored flowers with red-colored picotee petal margins and random spots and streaks; strong flowering stems; strong calyxes that resist splitting; good postproduction longevity with flowers maintaining good substance and color for about ten days in an interior environment after shipping; and resistance to *Fusarium oxysporum*.

2 Drawing Sheets

Botanical designation: *Dianthus caryophyllus*.
Cultivar denomination: 'Yoder Show'.

BACKGROUND OF THE INVENTION

The present invention relates to a new and distinct cultivar of Carnation plant, botanically known as *Dianthus caryophyllus* and hereinafter referred to by the name 'Yoder Show'.

The new Carnation is a product of a planned breeding program conducted by the Inventor in Salinas, Calif., and Madrid, Cundinamarca, Colombia, South America. The objective of the breeding program is to create new cut Carnation cultivars having long flowering stems, early flowering, attractive flower color and good flower form and substance.

The new Carnation originated from a cross-pollination made by the Inventor in 1998, in Salinas, Calif., of a proprietary selection of Carnation identified as code number 0753, not patented, as the female, or seed, parent, with a proprietary selection of Carnation identified as code number 0759, not patented, as the male, or pollen, parent.

The cultivar Yoder Show was discovered and selected by the Inventor as a flowering plant within the progeny of the stated cross-pollination in a controlled environment in Madrid, Cundinamarca, Colombia, South America in March, 2000. The selection of this plant was based on its flower color and good flower form and substance.

Asexual reproduction of the new Carnation by terminal cuttings in Madrid, Cundinamarca, Colombia, South America since April, 2000, has shown that the unique features of this new Carnation are stable and reproduced true to type in successive generations.

SUMMARY OF THE INVENTION

The cultivar Yoder Show has not been observed under all possible environmental conditions. The phenotype may vary somewhat with variations in environment such as temperature and light intensity without, however, any variance in genotype.

The following traits have been repeatedly observed and are determined to be the unique characteristics of 'Yoder Show'. These characteristics in combination distinguish 'Yoder Show' as a new and distinct cultivar of Carnation:

1. Large white-colored flowers with red-colored picotee petal margins and random spots and streaks.
2. Strong flowering stems.
3. Strong calyxes that resist splitting.
4. Good postproduction longevity with flowers maintaining good substance and color for about ten days in an interior environment after shipping.
5. Resistant to *Fusarium oxysporum*.

Plants of the new Carnation can be compared to plants of the female parent selection. In side-by-side comparisons conducted in Madrid, Cundinamarca, Colombia, South America, plants of the new Carnation and female parent selection differed in the following characteristics:

1. Plants of the new Carnation were taller than plants of the female parent selection.
2. Plants of the new Carnation flowered about one week later than plants of the female parent selection.
3. Plants of the new Carnation and the female parent selection differed in flower color as plants of the female parent selection had orange-colored flowers with red-colored stripes.

Plants of the new Carnation can be compared to plants of the male parent selection. In side-by-side comparisons conducted in Madrid, Cundinamarca, Colombia, South America, plants of the new Carnation and the male parent selection differed in the following characteristics:

1. Plants of the new Carnation were about 12 to 15 cm taller than plants of the male parent selection.
2. Plants of the new Carnation flowered about two weeks later than plants of the male parent selection.
3. Plants of the new Carnation and the male parent selection differed in flower color as plants of the male parent selection had light pink-colored flowers.

Plants of the new Carnation can also be compared to plants of the cultivar Farfalla, not patented. In side-by-side comparisons conducted in Madrid, Cundinamarca, Colombia, South America, plants of the new Carnation and the cultivar Farfalla differed in the following characteristics:

1. Plants of the new Carnation were about 20 to 25 cm taller than plants of the cultivar Farfalla.
2. Plants of the new Carnation flowered about one week earlier than plants of the cultivar Farfalla.
3. Plants of the new Carnation and the cultivar Farfalla differed slightly in flower color as plants of the cultivar Farfalla had less intense red-colored margins, spots and streaks.
4. Plants of the new Carnation were much more resistant to *Fusarium oxysporum* than plants of the cultivar Farfalla.

BRIEF DESCRIPTION OF THE PHOTOGRAPHS

The accompanying colored photographs illustrate the overall appearance of the new Carnation, showing the colors as true as it is reasonably possible to obtain in colored reproductions of this type. Colors in the photographs may differ slightly from the color values cited in the detailed botanical description, which accurately describe the colors of the new Carnation.

The photograph on the first sheet comprises a side perspective view of a typical flowering stem of 'Yoder Show' grown as a disbud or standard-type cut Carnation.

The photograph on the second sheet comprises a close-up view of a typical flower of 'Yoder Show'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Madrid, Cundinamarca, Colombia, South America under conditions which approximate commercial practice in a single-layer polyethylene-covered greenhouse. Four-week old rooted cuttings were planted in ground beds and pinched about three to four weeks later. During the production time, day temperatures ranged from 19° C. to 24° C.; night temperatures ranged from 4° C. to 12° C.; and light levels ranged from 3,000 to 5,000 foot-candles. Measurements and numerical values represent averages for six to ten typical flowering stems about 27 weeks after planting.

Botanical classification: *Dianthus caryophyllus* cultivar Yoder Show.

Commercial classification: Disbud or standard-type cut Carnation.

Parentage:

*Female, or seed, parent.*—Proprietary selection of *Dianthus caryophyllus* identified as code number 0753, not patented.

*Male, or pollen, parent.*—Proprietary selection of *Dianthus caryophyllus* identified as code number 0759, not patented.

Propagation:

*Type.*—Terminal tip cuttings.

*Time from sticking unrooted cuttings to planting.*—About four weeks.

*Root description.*—Fine, freely-branching.

Plant description:

*Flowering stem description.*—Length: About 91 to 93 cm. Diameter: About 7 mm. Aspect: Erect. Strength: Very strong, flexible. Internode length: About 11.3 cm. Texture: Smooth, glabrous; waxy. Color: Close to 147A, overlain with waxy bloom, close to 188A to 188C.

*Foliage description.*—Arrangement: Opposite; sessile. Aspect: Concave; mostly upright to eventually reflexing and curling. Length: About 12.75 cm. Width: About 1.3 cm. Shape: Linear. Apex: Sharply acute to acuminate. Base: Clasping. Margin: Entire. Texture, upper and lower surfaces: Tough, leathery; waxy. Venation: Parallel. Color: Developing foliage, upper and lower surfaces: Close to 147A, overlain with waxy bloom, close to 188A to 188B. Fully developed foliage, upper and lower surfaces: Close to 147A; overlain with waxy bloom, close to 188A to 188B. Venation, upper and lower surfaces: Similar to lamina.

Flowering description:

*Appearance.*—Large single hemispherical flowers; typically grown as a disbud or standard-type with one flower per stem.

*Flowering response.*—Year-round under greenhouse conditions; plants flower about 27 weeks after planting rooted cuttings.

*Postproduction longevity.*—Good postproduction longevity with flowers maintaining good substance and color for about ten days in an interior environment after shipping. Flowers persistent.

*Fragrance.*—Slightly fragrant; spicy, clove-like.

*Flower size.*—Diameter: About 7.2 cm. Depth (height): About 4.7 cm.

*Petals/petaloids.*—Quantity per flower: About 62, imbricate. Length: About 4.8 cm. Width: About 2.75 cm. Shape: Roughly spatulate to fan-shaped. Apex: Roughly rounded; finely serrated giving a fringed appearance; undulate. Lateral margins: Entire. Texture, upper and lower surfaces: Smooth, glabrous; velvety. Color: When opening and fully opened, upper surface: Close to 155D; towards the margin and random spots and streaks, close to 53A. When opening and fully opened, lower surface: Close to 155D; towards the margin and random spots and streaks, close to 53A.

*Sepals.*—Quantity: About six, fused. Length: About 3 cm. Calyx diameter: Apex: About 2.2 cm. Base: About 1.6 cm. Shape: Roughly linear. Apex: Acuminate. Texture, upper and lower surfaces: Tough, leathery; smooth; waxy, longitudinally ridged. Resistance to splitting: Very good, calyxes resist splitting. Color: Upper surface: Close to 195B. Lower surface: Close to 144A to 146B.

*Reproductive organs.*—Androecium: Stamen number: About twelve. Anther length: About 2 mm. Anther shape: Oblong. Anther color: Close to 158A. Pollen: None observed. Gynoecium: Pistil quantity: About two to four. Style length: About 1.9 cm. Style color: Close to 155D. Stigma shape: Linear. Stigma color: Close to 155D. Ovary size: About 1 cm by 7.5 mm. Ovary color: Base, close to 155D; apex, close to 151D.

*Seed/fruit.*—Seed and fruit production have not been observed.

Disease/pest resistance: Plants of the new Carnation planted in soils heavily infested with *Fusarium oxysporum* have been observed to be highly resistant to *Fusarium oxysporum*. Plants of the new Carnation have not been observed to be resistant to other pathogens and pests common to Carnations.

It is claimed:

1. A new and distinct cultivar of Carnation plant named 'Yoder Show', as illustrated and described.

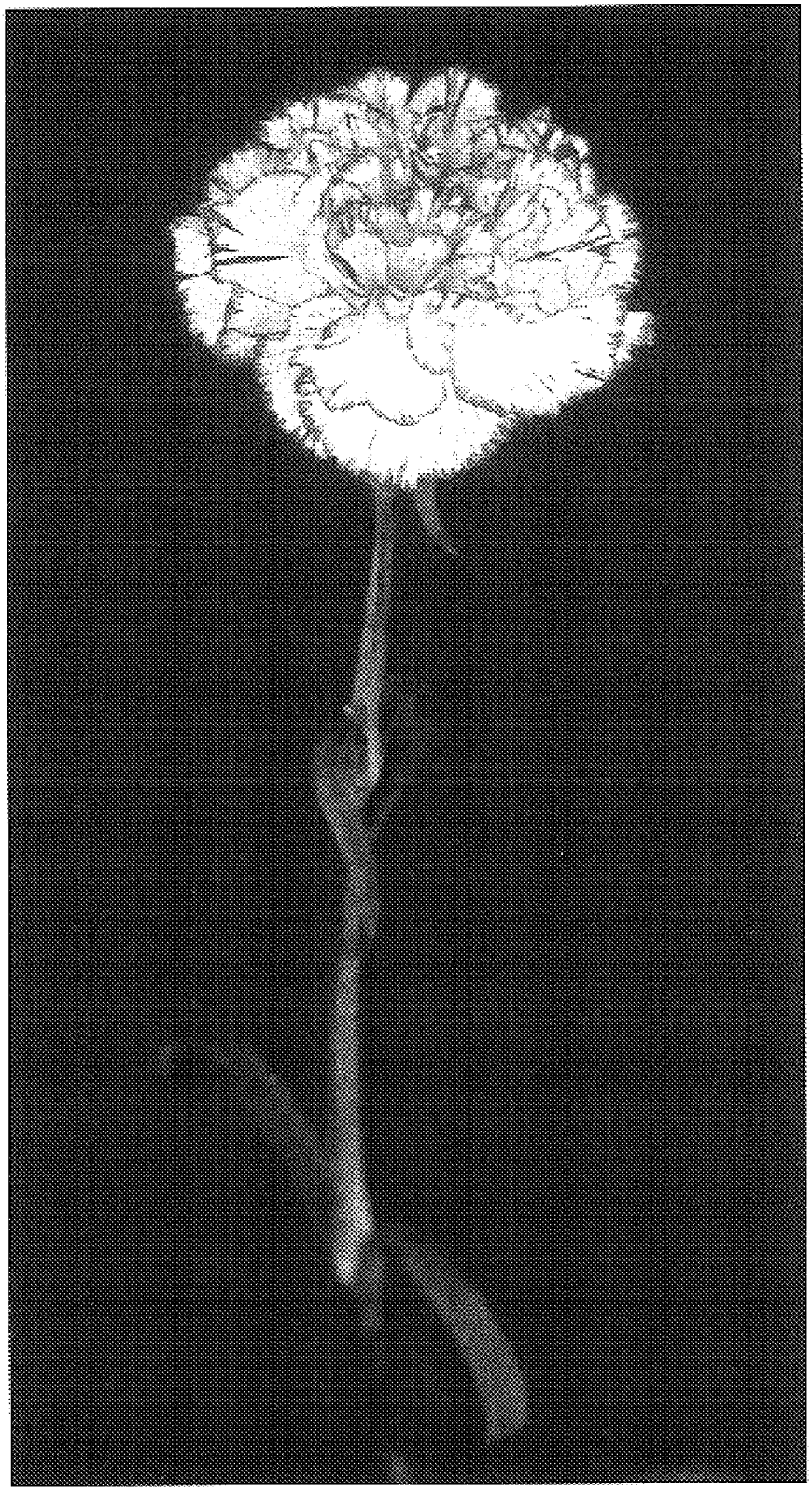

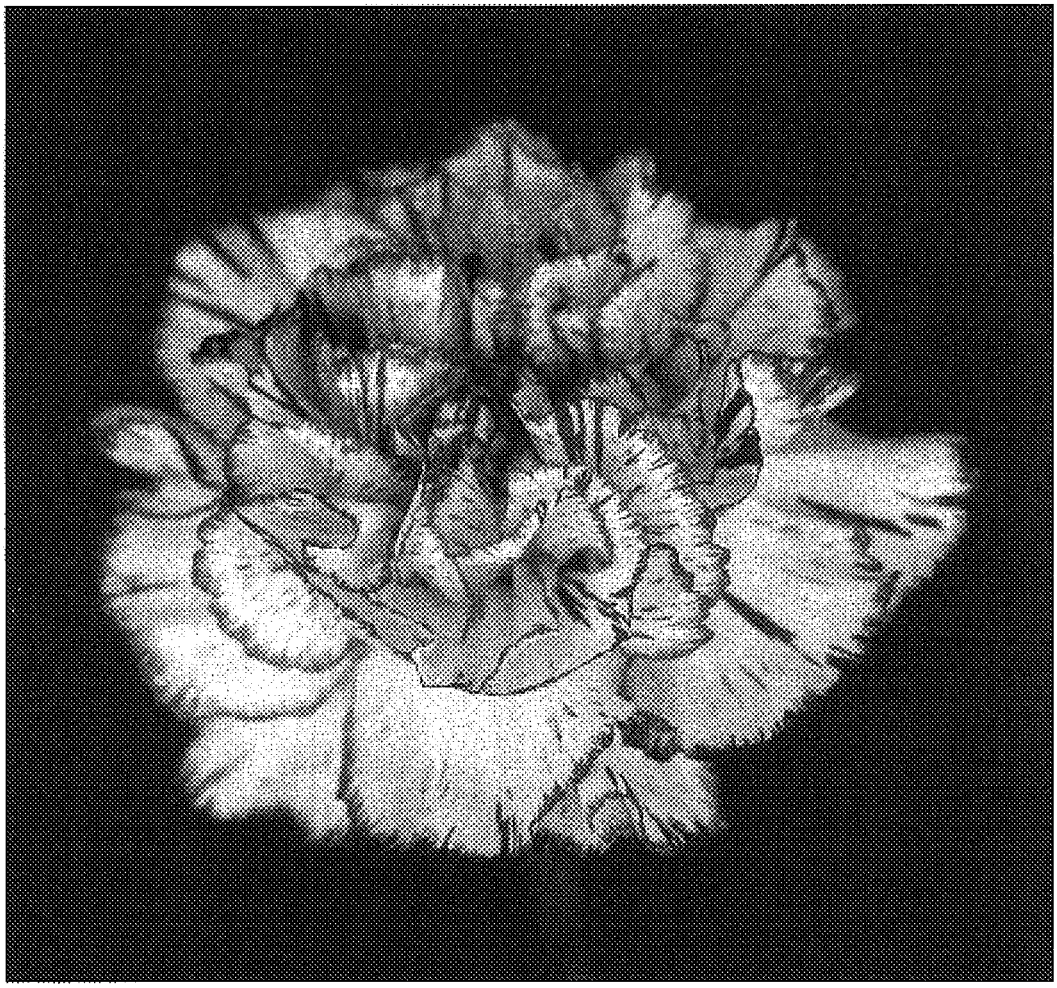

* * * * *